United States Patent [19]
Kao et al.

[11] Patent Number: 5,981,817
[45] Date of Patent: Nov. 9, 1999

[54] XYLENE ISOMERIZATION PROCESS

[75] Inventors: Jar-Lin Kao, Houston, Tex.; Greg J. De Martin, Bogota; Stuart Leon Soled, Pittstown, both of N.J.

[73] Assignee: Exxon Chemical Patents Inc., Houston, Tex.

[21] Appl. No.: 08/844,051

[22] Filed: Apr. 10, 1997

[51] Int. Cl.$^6$ ........................................... C07C 5/27
[52] U.S. Cl. .................................. 585/481; 585/480
[58] Field of Search ................................. 585/480, 481

[56] References Cited

U.S. PATENT DOCUMENTS

| | | | |
|---|---|---|---|
| 4,283,584 | 8/1981 | Chester et al. | 585/481 |
| 4,331,822 | 5/1982 | Onodera et al. | 585/482 |
| 4,584,423 | 4/1986 | Nacamuli et al. | 585/481 |
| 4,695,666 | 9/1987 | Chao et al. | 585/481 |
| 4,962,258 | 10/1990 | Amesle et al. | 585/480 |
| 5,030,788 | 7/1991 | Amelse et al. | 485/480 |
| 5,476,823 | 12/1995 | Beck et al. | 502/60 |
| 5,574,199 | 11/1996 | Beck et al. | 585/407 |

*Primary Examiner*—Glenn Caldarola
*Assistant Examiner*—Thuan D. Dang
*Attorney, Agent, or Firm*—Edward F. Sherer

[57] ABSTRACT

A process for isomerizing a nonequilibrium xylene feed mixture is disclosed. The isomerization is conducted in the presence of hydrogen and at pressures in excess of 75 psig over a ZSM-5 type catalyst containing about 0.1 to 5 wt % of at least one metal selected from the group consisting of zinc, copper, silver and gallium. In another embodiment, the catalyst may further contain an oxide of at least one element selected from silicon, germanium and tin. The process produces a product containing about or above equilibrium quantities of para-xylene with low xylene loss.

15 Claims, 1 Drawing Sheet

XYLENE ISOMERIZATION PROCESS

BACKGROUND OF THE INVENTION

1. Field of the Invention

This invention relates to an improved process for the isomerization of ortho- and meta-xylenes to para-xylene, as well as removal of ethylbenzene from the $C_8$ aromatics stream.

2. Description of Related Art

Catalytic reforming hydrocarbon feeds such as naphtha using conventional aromatization catalysts produces reformate which is richer in the content Of $C_6$–$C_{10}$ aromatics than the feeds. Of these aromatics, significant quantities of $C_8$ aromatics are produced which comprise a mixture of ethyl benzene, and mixed ortho-, meta- and para-xylene isomers. Typically, the product from the catalytic reformer (reformate) is fed to an aromatic extraction plant where the aromatics, e.g. $C_6$, $C_7$ and $C_8$ aromatics, are separated from the paraffins and other non-aromatic products present in the reformate. The $C_8$ aromatic fraction may then be separated from the lower boiling $C_6$ and $C_7$ aromatics by distillation.

The $C_8$ aromatic fraction normally contains a mixture of ethyl benzene and the ortho, para and meta xylene isomers. The three xylene isomers are usually present in near thermodynamic equilibrium amounts, e.g., generally 52–53 wt % meta xylene, 23–24 wt.% para xylene and 23.5 to 24.5 wt % ortho xylene. Because para-xylene is a more valuable isomer used as a chemical intermediate in a number of applications, it may be desirable to separate the para-xylene from the other isomers using conventional techniques such as crystallization, or by adsorption/desorption on zeolites. After such separation, the residual $C_8$ aromatic fraction contains non-equilibrium quantities of ethyl benzene and the mixed ortho and meta-xylene isomers and is lean with respect to para-xylene content.

The para-xylene lean residual product may be further upgraded by subjecting it to isomerization conditions wherein at least a portion of the ethyl benzene undergoes a hydrogenolysis reaction to benzene and ethane and a portion of the ortho and meta xylenes are isomerized to produce a mixture which once again approximates the equilibrium concentration of the ortho, meta and para xylene isomers. Typically such isomerization conditions comprise contacting the non-equilibrium $C_8$ aromatic feed with a suitable isomerization catalyst, such as a molecular sieve, in a suitable reactor at temperatures above about 700° F. and at pressures sufficient to maintain the reaction in the vapor phase.

Numerous catalysts have been proposed for use in the isomerization process. For example, U.S. Pat. No. 4,331,822 discloses vapor phase isomerization in the presence of added hydrogen using a crystalline aluminosilicate zeolite such as ZSM-5 wherein the catalyst contains two different metals, one being platinum and the other being a metal inclusive of metals such as zinc. However, a disadvantage associated with the use of noble metals such as platinum in such processes, besides the expense of such metals, is that use of the platinum loaded catalyst can lead to a substantial loss of xylenes during the isomerization reaction as a consequence of acid-catalyzed trans-alkylation reactions and ring cracking reactions. Also, platinum-containing catalysts require a more complicated and time consuming regeneration process after they are at least partially deactivated as the result of coke build-up on the catalyst surface.

Another isomerization process disclosed in U.S. Pat. No. 4,584,423 involves the use of a zeolite catalyst such as ZSM-5 which is loaded with 0.05 up to 1.5 weight percent of a metal selected from the group consisting of zinc, cadmium, iron, barium, tin and cesium. The process is conducted in the absence of added hydrogen and at relatively low pressures below about 100 psig. The process is demonstrated to produce relatively low xylene loss in the range of about 1.21 to about 2.65 percent at a relatively high ethyl benzene conversion rate.

However, a disadvantage of such a process conducted without the use of added hydrogen and at relatively low pressure is that the catalyst tends to more quickly deactivate due to coke build-up thereby shortening run lengths.

SUMMARY OF THE INVENTION

The present invention provides a process for isomerizing a non-equilibrium feed mixture containing xylene isomers comprising contacting said feed mixture in a reaction zone under xylene isomerization conditions with a catalyst comprising an intermediate pore size crystalline aluminosilicate support containing from about 0.1 to about 5 wt % of at least one metal selected from the group consisting of zinc, copper, silver and gallium, and producing an isomerized product, said xylene isomerization conditions including the presence of added hydrogen at a level of at least about 0.1 mole hydrogen per mole of said feed mixture and a reactor pressure of greater than about 75 psig.

In another embodiment of the invention, the catalyst used in the isomerization process further contains an oxide of at least one element selected from the group consisting of silicon, germanium and tin.

The isomerization of $C_8$ aromatic streams using the catalysts and in accordance with the process of this invention gives rise to an isomerization product which contains about equilibrium quantities or above of para-xylene with a very low percent of xylene loss. In addition, the development of $C_3$ to $C_5$ hydrocarbons due to ring cracking reactions during isomerization is markedly reduced.

DETAILED DESCRIPTION OF THE INVENTION

Figure 1:
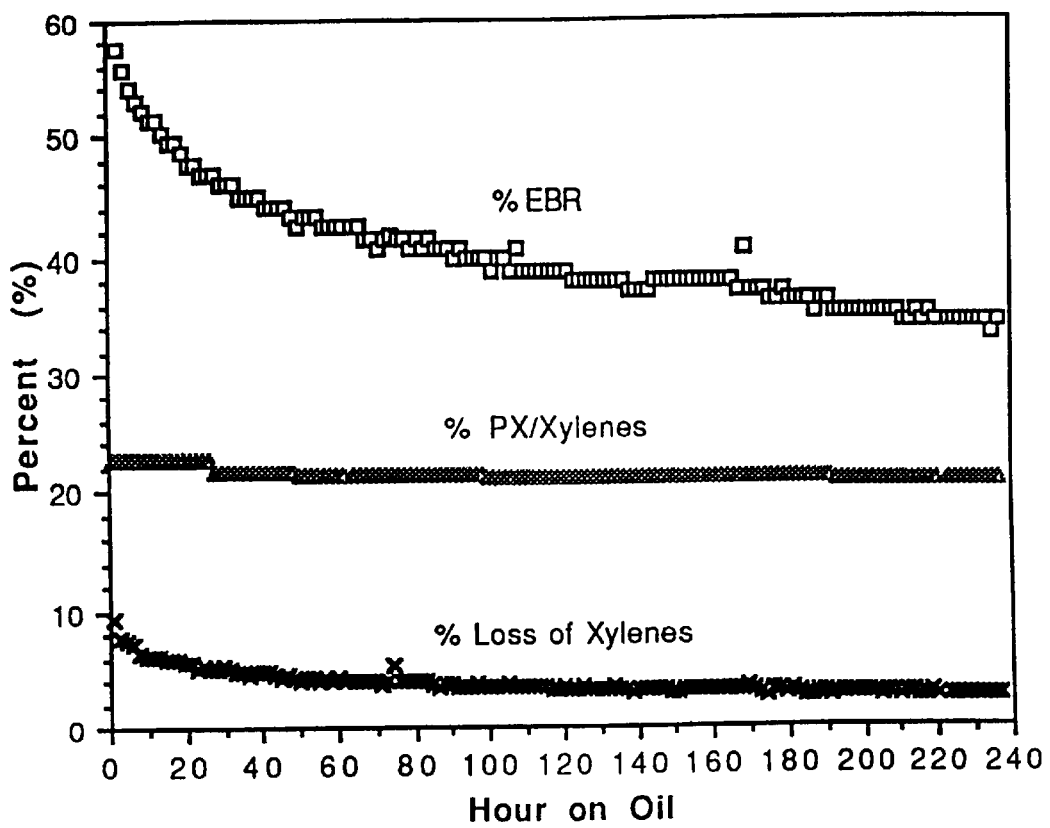
FIG. 1 is a graph plotting the % loss of xylenes, % para-xylene produced and % ethylbenzene removal vs. isomerization time of Example 5.

Crystalline aluminosilicates which may be used as molecular sieve support material for the catalyst of the present invention include intermediate pore size zeolites having an average pore size in the range of about 5 to 7 Angstroms and a $SiO_2/Al_2O_3$ ratio of at least 10. These include zeolites having a MFI, MEL, TON, MTT or FER crystalline structure. Preferred such zeolites include ZSM-5, silicalite (a high silica to alumina ratio form of ZSM-5), ZSM-1 1, ZSM-1 2, ZSM-21, ZSM-22, ZSM-23, ZSM-35 and ZSM-38, with ZSM-5 being most preferred. The zeolite is preferably used in its highly acidic form, e.g. HZSM-5. Where the zeolite, as synthesized, contains alkali or alkaline earth metal cations, these can be exchanged with ammonium cations, followed by calcination in air at 600° F. to 1000° F. for about 1–10 hours by techniques well known in the art to produce the acid form of the zeolite.

The metals loaded into the catalyst appear to serve the same role as the noble metals of the prior art, e.g. hydrogenolysis agents, but result in significantly lower loss of xylenes during the isomerization process. Suitable metals are zinc, copper, silver and gallium. The metals may be incorporated into the zeolite structure by any suitable well known methods such as impregnation (incipient wetness method) or by ion exchange.

In the preferred embodiment, the zeolite is impregnated with the metal by well known methods such as by contacting a solution of metal salt dissolved in an aqueous or alcoholic medium with the zeolite particles for a period of time sufficient to allow the cations to penetrate the zeolite pore structure. Suitable salts include the acetates, chlorides and nitrates. After drying the resulting zeolite precursor, it is preferably calcined in air at temperatures of 300° F.–1000° F. for a period of 1–24 hours. In most cases, the metal will be present in the post-calcined zeolite structure in the form of the metal oxide. The preferred metal loading ranges from about 0.1 to about 5 wt %, more preferably from about 0.2 to 2.5 wt % metal based on the weight of the zeolite.

In another embodiment of the invention, the aluminosilicate support may further contain an oxide of at least one element selected from the group consisting of silicon, germanium and tin. The presence of this second element has been found to further reduce the acidity of the aluminosilicate support producing even less xylene loss and a lower degree of ring cracking to $C_3$–$C_5$ hydrocarbons and a somewhat higher degree of ethyl benzene conversion during the isomerization process.

Where the second element is a metal, i.e., germanium or tin, it can be incorporated into the zeolite by the same methods described above with respect to zinc, copper, silver and gallium incorporation, either before or after such incorporation. Where the second element is silicon, is preferably applied to the zeolite already impregnated with the first metal by forming a mixture of the metal-impregnated zeolite and an inorganic or organosilicon compound or solution of such compound, drying the mixture and calcining the mixture in air at 300° F.–1000° F. for a period of 2–24 hours to reduce the silicon to the oxide state, e.g., $SiO_2$.

Organosilicon compounds which may be used to provide a source of silicon include compounds selected from the group consisting of silanes, silicones, and alkylsilicates. Suitable silanes include alkoxy silanes such as tetramethoxy or tetraethoxy silane. Suitable silicones and silicone polymers include compounds having the formula —$[R_1R_2SiO]_n$ wherein $R_1$ and $R_2$ are the same or different $C_1$ to $C_4$ alkyl groups, phenyl groups, halogen, hydrogen, hydroxy, alkoxy, aralkyl and the like with at least one of $R_1$ or $R_2$ being an organic group, and n ranges from 2 to 1,000. Examples of such silicones include dimethylsilicone, dimethylsiloxane-ethylene oxide block copolymers, diethyl-silicone, methyl hydrogen silicone and the like. Suitable alkyl silicates include $C_1$ to $C_4$ alkyl silicates such as methyl silicate or ethyl silicate.

Suitable inorganic silicon-containing compounds which may be used to provide a source of silicon include alkali or alkaline earth metal silicates, e.g., sodium silicate.

The silicon compound is preferably deposited on the surface of the zeolite such that it tends to block some of the remaining free acid sites present on the surface of the zeolite and on the surfaces of the channels present within the zeolite structure. For example, the silicon compound may be dissolved or dispersed in a solvent or aqueous medium to form a solution, dispersion or emulsion, or used neat where it is a liquid, mixed with the aluminosilicate to form a paste, dried and calcined. Alternatively, the silicon compound may be deposited on the zeolite aluminosilicate surface by well known vapor deposition techniques.

In some cases it may be desirable to repeat the silicon compound coating process, i.e., coating, drying and calcining, one or more times to provide a more uniform application of the silicon-containing compound on the zeolite surfaces.

The oxide of silicon, germanium or tin is present in the aluminosilicate support at a level of from about 0.5 to 50 wt %, more preferably from about 1 to 30 wt %, based on the weight of the aluminosilicate support.

The aluminosilicate may be used in the catalytic process in its crystalline particulate form or it may be combined with 10–50 wt % of a binder material such as silica, alumina or various clay materials as is known in the art to form particles such as molded pills or extrudates. The metal impregnation process described above may be carried out before or after the aluminosilicate is composited with the binder, but preferably before. The zeolite may also be used in the form of zeolite-bound particles such as prepared in accordance with U.S. Pat. No. 5,460,796, the disclosure of which is incorporated herein by reference.

In the preferred embodiment of the invention, the metals loaded into the aluminosilicate support consist essentially of one or more of the metals described above and do not include noble metals such as platinum, platinum/rhenium or platinum/iridium which tend to be more sensitive to deactivation by sulfur poisoning and/or coke build-up under isomerization conditions, and which tend to produce more ring cracking of the aromatic compounds during isomerization.

The aromatic hydrocarbon feed mixture used in the isomerization of xylenes in this invention predominantly contains xylene isomers which have not attained a thermodynamic equilibrium composition. As is well known, xylene contains three isomers, ortho-, meta- and para-isomers. It is known that when a mixture in an arbitrary ratio of the three isomers is subjected to an isomerization reaction, the reaction reaches an equilibrium when the ratio among the three isomers attains a certain specific value, and apparently no further advance of the isomerization is noted. The composition of the xylene isomers at such an equilibrium state is called the "thermodynamic equilibrium composition."

The aromatic hydrocarbon feed mixture to be used as a starting material in the process of this invention may consist only of the xylene isomers, or may be a mixture of the xylene isomers with another aromatic hydrocarbon such as ethylbenzene, benzene, toluene, ethyltoluene, trimethylbenzene, diethylbenzene, ethylxylene, and tetramethylbenzene. In the latter case, the xylene isomeric mixture is present desirably in an amount of generally at least 30% by weight, preferably at least 50% by weight, based on the weight of the aromatic hydrocarbon feed.

The $C_8$ aromatic hydrocarbon fractions obtained by reforming, thermal cracking or hydrocracking of naphtha can be used especially advantageously as the aromatic hydrocarbon feed in the process of this invention. These fractions contain ethylbenzene of the same number of carbons in addition to the xylene isomers. Very good results can be obtained in the process of this invention when using a $C_8$-aromatic hydrocarbon fraction which contains the xylene isomers and ethylbenzene in a total amount of at least 80%, preferably at least 90% by weight, based on the weight of the feed.

The isomerization process may be carried out in the vapor phase using a fixed bed, fluid bed or membrane reactor system. Preferably the reaction is conducted by passing the feed through a fixed bed pressure reactor packed with the isomerization catalyst described above and under the following conditions:

|  | General | Preferred |
| --- | --- | --- |
| Temperature (° F.) | 650–1000 | 700–900 |
| Pressure (psig) | >75–600 | >100–500 |
| WHSV | 1–500 | 2–50 |
| $H_2$/Feed Mole Ratio | 0.1–10 | 0.5–5 |

Where the reaction is conducted at higher pressures above about 200 psig, a lower hydrogen feed molar ratio in the range of from 0.1 to 1.5 is preferred.

The following examples are illustrative of the invention.

EXAMPLE 1

A HZSM-5 catalyst was prepared by calcining commercial ZSM-5 sample (80 $SiO_2/Al_2O_3$ from UCI) at 932° F. for 4 hr. A 1.5 wt % ZnZSM-5 catalyst precursor was prepared by impregnating 40.33g of HZSM-5 powder with solution of 2.7628g of $Zn(NO_3)_2$ and 37.97g of water. After drying at 248° F. for 2 hr., the catalyst precursor was calcined at 932° F. for 4 hr. to give a ZnO/HZSM-5 catalyst (i.e. ZnZSM-5).

EXAMPLE 2

The ZnZSM-5 catalyst (25.93g) of Example 1 was mixed with 30.64 g of a liquid dimethylsiloxane-ethylene oxide copolymer. The wet paste was placed in a vacuum at 140° F. for 4 hr. and calcined at 986° F. for 8 hr. to give a silica coated ZnZSM-5 catalyst [i.e., 1×(Si)ZnZSM-5]. The above silica-coating procedure was repeated 3 more times to give a 4×(Si)ZnZSM-5 catalyst. Prior to the catalytic test, the powder catalyst was pelletized and crushed to 16/45 mesh particles.

COMPARATIVE EXAMPLE 3

A 0.1% Pt/HZSM-5 catalyst was prepared by impregnating 29.87g of dry HZSM-5 used in Example 1 with 28.12g of a Pt loading stock solution containing 0.05940g of $Pt(NH_3)_4(NO_3)_2$. After aging for 0.5 hr., the catalyst was dried in vacuum at 248° F. for 2 hr. and calcined at 662° F. for 2 hr.

EXAMPLE 4

A series of isomerization reactions were conducted using various catalysts including the catalyst of this invention by passing an artificial feed containing 12.9 wt % ethyl benzene (EB), 62 wt % of meta xylene (MX), 20.6 wt % ortho xylene (OX), 1.3 wt % para xylene (PX) and 3.2 wt % toluene through a fixed bed of different catalysts identified in Table 1 under the following conditions:

Temperature—800° F.

Pressure—200 psig

WHSV—8

$H_2$/feed mole ratio—2

Run Time—20 hrs.

Table 1 summarizes the experimental results and distribution of aromatics as measured by gas chromatography, for each of five experiments.

TABLE 1

| Exp. | Catalyst Type | % EB Conv. | Xylenes Loss(%) | Ring Cracking to $C_3$–$C_5$ | % Isomer in Xylenes | | | % of Equilibrium |
| --- | --- | --- | --- | --- | --- | --- | --- | --- |
|  |  |  |  |  | MX | PX | OX | PX |
| A | 4 × (Si) ZnZSM-5 | 74.2 | 0.9 | 0.4 | 53.8 | 23.3 | 22.9 | 99.1 |
| B | ZnZSM-5 | 67.5 | 1.3 | 0.5 | 51.5 | 25.1 | 23.4 | 106.5 |
| C | Pt/HZSM-5 | >99.9 | 11.9 | 3.1 | 52.7 | 24.1 | 23.1 | 102.6 |
| D | HZSM-5 | 92.9 | 12.5 | 2.5 | 52.6 | 24.1 | 23.3 | 102.6 |
| E | Isoxyl EX720 | 66.3 | 5.9 | 1.2 | 53.0 | 23.5 | 23.5 | 100.0 |
|  | Equil. | — | — | — | 52.5 | 23.5 | 24.0 | 100.0 |

In experiment A, the catalyst of Example 2 was used and in experiment B, the catalyst of Example 1 was used. In experiment C, the platinum-containing catalyst prepared in accordance with Comparative Example 3 was used. In experiment D, a non modified HZSM-5 commercially available from UCI was employed while in experiment E, a commercial isomerization catalyst from Sud Chemie was employed (Isoxyl EX720, a 1/16"×1/4" alumina bound HZSM-5 extrudate).

As shown in Table 1, % EB conversion is determined by the formula: % EB Conv=100×[EB in-EB out] divided by EB in; loss of xylenes is determined by the formula: xylenes loss (%)=[$A_7$ in–$A_7$ out+$A_e$ out+$A_{10}$ out] where $A_7$, $A_e$ and $A_{10}$ represent aromatics containing 7, 9 and 10 carbon atoms respectively; and % of Equilibrium PX=100×(PX) experimental divided by the equilibrium PX.

The data in Table 1 show that although the Pt/HZSM-5 and HZSM-5 catalysts show higher activity in removing EB than those obtained in Expts. A and B, both catalysts give substantially higher xylene loss than those observed in Expts. A and B, (i.e. the invention). Low xylene loss is one of the major criteria for selecting an XY isomerization catalyst in commercial operation. Expts. A and B are examples of this invention showing lower xylenes loss and higher EB removal than those observed in the commercial catalyst (i.e. Isoxyl EX720). Also, the Pt loaded catalysts show higher xylenes loss and ring cracking activity than the ZnO loaded catalysts.

Table 1 also shows the that the catalyst used in Expt. B provides a higher quantity of para-xylene than the other catalysts evaluated. The catalyst used in Expt. A gave a slightly lower quantity of para-xylene, but it provides lower xylene loss than the prior art catalysts and the catalyst of Expt. B, and also a slightly lower degree of ring cracking.

One of the major routes accounting for xylene loss is trans-alkylation during isomerization. As evidenced by the GC analysis of the isomer products produced, prior art catalysts with high xylene loss (Expts. C, D and E) produce more $C_9$–$C_{10}$ aromatics, e.g. trimethylbenzenes, ethyltoluenes and diethylbenzenes.

EXAMPLE 5

This example demonstrates the long term stability of a Zn loaded ZSM-5 extrudate (i.e. binder-free ZSM-5) under commercial reaction conditions.

A mixtures of 2.73 g of $Zn(NO_3)_2$, 29.70 g of water and 30.31 g of binder-free ZSM-5 extrudate (~1/8"×1/4") of the type prepared in U.S. Pat. No. 5,460,796 was placed in a covered bottle and aged at 122° F. for 21 hr. After drying in vacuum at 250° F. for 2hr, the Zn loaded extrudate was calcined at 932° F. for 4hr to give 31.15 g of catalyst.

A plant feed containing toluene (0.6%), ethylbenzene (11.3%), m-xylene (65.3%), o-xylene (20.0%) and p-xylene (2.7%) and $C_9$-aromatics (0.1%) was used to test the stability of the above catalyst under the conditions of 700° F., 250 psig, 10 WHSV and 1, $H_2$/feed over a period of 237 hr. As can be seen in FIG. 1 after 60 hr for the line-up, this catalyst always gave about 21–22% of p-xylene in total xylenes and low loss of xylenes (3–5%), while maintaining >35% of ethylbenzene removal (EBR) over a period of about 240 hours.

COMPARATIVE EXAMPLE 6

Experiment B in Table 1 was repeated using the Zn ZSM-5 catalyst of Example 1 except that the isomerization reaction was conducted under nitrogen and in the absence of hydrogen gas. Test conditions were as follows: Temp—800° F.; 8 WHSV; Pressure—200 psig; Time—20 hrs; and $N_2$/feed mole ratio—2. Test results as compared with run B of Table I are shown in Table 2.

TABLE 2

| Gas Type | % EB Conv. | Xylene Loss (%) | Ring Cracking | % Isomer In Xylene | | | % of PX Equilibrium |
|---|---|---|---|---|---|---|---|
| | | | | MX | PX | OX | |
| $N_2$ | 37.2 | 1.6 | 0.0 | 52.8 | 23.9 | 23.3 | 102.7 |
| $H_2$ | 67.5 | 1.3 | 0.5 | 51.5 | 25.1 | 23.4 | 106.8 |

As can be seen from Table 2, the catalyst deactivated rapidly under nitrogen yielding only 37.2% ethylbenzene conversion after 20 hours in contrast with 67.5% ethyl benzene conversion under hydrogen.

What is claimed is:

1. A process for isomerizing a non-equilibrium feed mixture containing at least 30 wt. % xylene isomers comprising contacting said feed mixture in a reaction zone under xylene isomerization conditions with a platinum-free catalyst consisting essentially of an intermediate pore size crystalline aluminosilicate support containing from about 0.1 to about 5 wt % of at least one impregnated metal selected from the group consisting of zinc, copper, silver and gallium and producing an isomerized product, said xylene isomerization conditions including the presence of added hydrogen at a level of at least about 0.1 mole hydrogen per mole of said feed mixture and a reactor pressure of greater than about 75 psig.

2. The process of claim 1 wherein said aluminosilicate support is ZSM-5 zeolite.

3. The process of claim 1 wherein said metal is zinc.

4. The process of claim 1 wherein said isomerization conditions include a system pressure of greater than 100 up to about 500 psig, a hydrogen: feed mixture mole ratio of from 0.1 up to about 10, a weight hourly space velocity of from about 1 to about 500 and an isomerization temperature in the range of about 650° to 1000° F.

5. The process of claim 1 wherein said aluminosilicate support further contains an oxide of at least one element selected from the group consisting of germanium and tin.

6. The process of claim 5 wherein said oxide is present in said aluminosilicate support at a level of from about 0.5 to 50 wt %.

7. The process of claim 5 wherein said aluminosilicate support is ZSM-5 zeolite.

8. The process of claim 7 wherein said metal is zinc and said oxide is silica.

9. The process of claim 1 wherein said feed mixture comprises a mixture of ortho-xylene and meta-xylene and the xylenes are isomerized to para-xylene.

10. The process of claim 1 wherein said catalyst comprises zeolite particles held together with a binder material selected from the group consisting of silica, alumina, zeolite and clay.

11. The process of claim 1 wherein said catalyst comprises zeolite-bound particles.

12. The process of claim 1 wherein said aluminosilicate support further contains an oxide of silicon deposited on the surfaces thereof.

13. The process of claim 12 wherein said oxide of silicon is deposited on the surface of said aluminosilicate support by contacting said support with a silicon-containing compound sufficient to coat said support, and calcining said coated support in air at a temperature of at least 300° F., sufficient to reduce the silicon to the oxide state.

14. The process of claim 13 wherein said silicon-containing compound is an organosilicon compound.

15. The process of claim 12 wherein said oxide of silicon is present on the surfaces of said support at a level of from about 0.5% to 50 wt. %.

* * * * *